US005414508A

United States Patent [19]
Takahashi et al.

[11] Patent Number: 5,414,508
[45] Date of Patent: May 9, 1995

[54] OPTICAL CELL AND OPTICAL DETECTION SYSTEMS LIGHT ABSORPTION

[75] Inventors: Satoshi Takahashi, Kokubunji; Hideki Kambara, Hachiouji, both of Japan

[73] Assignee: Hitachi, Ltd., Tokyo, Japan

[21] Appl. No.: 25,232

[22] Filed: Mar. 2, 1993

[30] Foreign Application Priority Data

Mar. 2, 1992 [JP] Japan .................. 4-044394

[51] Int. Cl.$^6$ ............... G01N 21/05; G01N 15/02
[52] U.S. Cl. .................. 356/246; 356/440; 356/344
[58] Field of Search ........... 356/244, 246, 436, 440, 356/344; 250/461.2

[56] References Cited

U.S. PATENT DOCUMENTS

| | | | |
|---|---|---|---|
| 4,348,107 | 9/1982 | Leif | 356/317 |
| 4,455,089 | 6/1984 | Yeung et al. | 356/352 |
| 4,523,841 | 6/1985 | Bronsting et al. | 356/343 |
| 4,750,837 | 6/1988 | Gifford et al. | 356/417 |
| 5,104,218 | 4/1992 | Garner | 356/244 |
| 5,125,742 | 6/1992 | Wilks, Jr. | 356/440 |
| 5,250,186 | 10/1993 | Dollinger et al. | 356/369 |

OTHER PUBLICATIONS

Wang et al., "Nanoliter–Scale Multireflection Cell for Absorption Detection in Capillary Electrophoresis", American Chemical Society, vol. 63, No. 14 (1991) 1372–1376.

Gould, John H., "Construction and Use of Reflecting Multiple–Pass Absorption Cells for the Ultraviolet, Visible and Near Infrared", Applied Spectroscopy, Jan./Feb. 1971, vol. 25, No. 1, pp. 103–105.

*Primary Examiner*—Robert P. Limanek
*Assistant Examiner*—David B. Hardy
*Attorney, Agent, or Firm*—Antonelli, Terry, Stout & Kraus

[57] ABSTRACT

An optical cell or an optical detection system, of a simple structure having a small light path length, such as, for example, an optical cell having a light path length equal to that of a capillary. Light incidence and exit surfaces of the optical cell are each formed by a half transmitting mirror, and light is made incident on the optical cell in a direction perpendicular to the cell. The reflectance of the half transmitting mirror formed at the incidence surface is set smaller than that of the half transmitting mirror formed at the exit surface. The said optical cell or optical detection system is used as an optical detector portion of a sample separation and detection system which is for separation and detection of a sample using a liquid chromatography system or an electrophoresis system. Because of multi-reflection of light between both half transmitting mirrors, an effective increase of absorbance is obtained and even a sample whose absorbance is not higher than the noise level can be detected easily in high sensitivity. Further, since even a low concentration of sample does not cause lowering in the intensity of fluorescence, it is possible to detect both absorbance and fluorescence simultaneously.

16 Claims, 7 Drawing Sheets

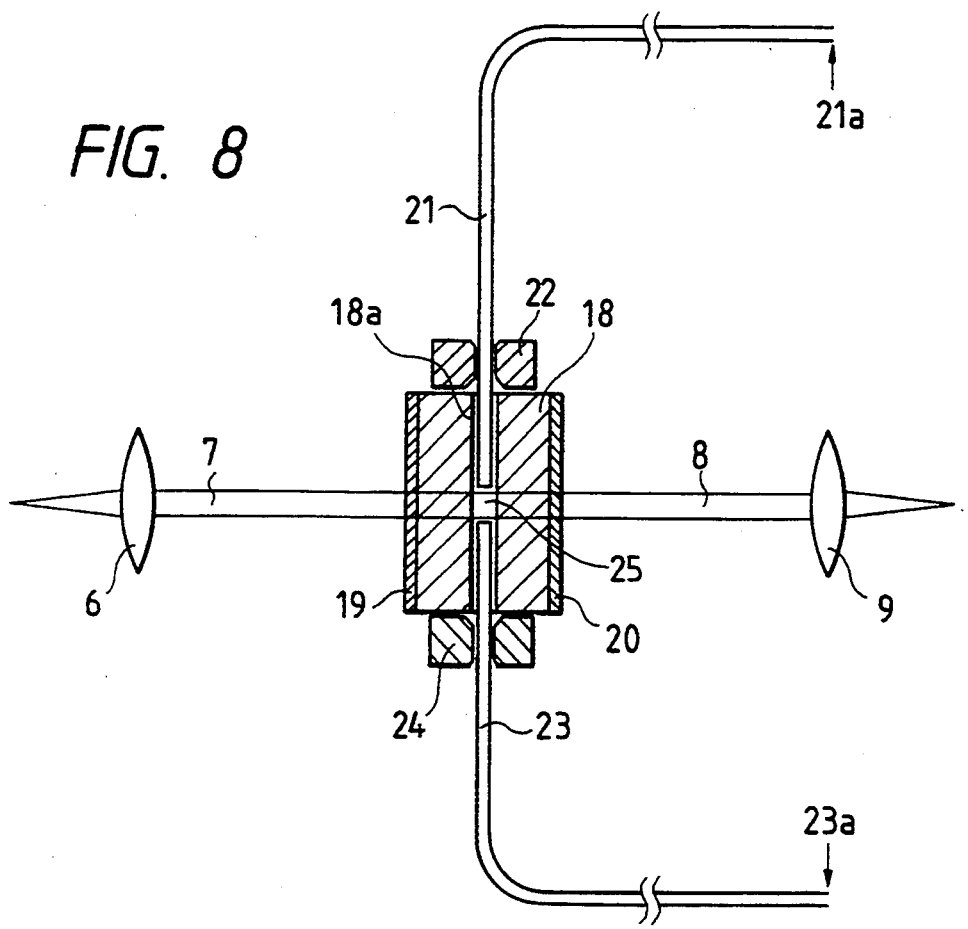
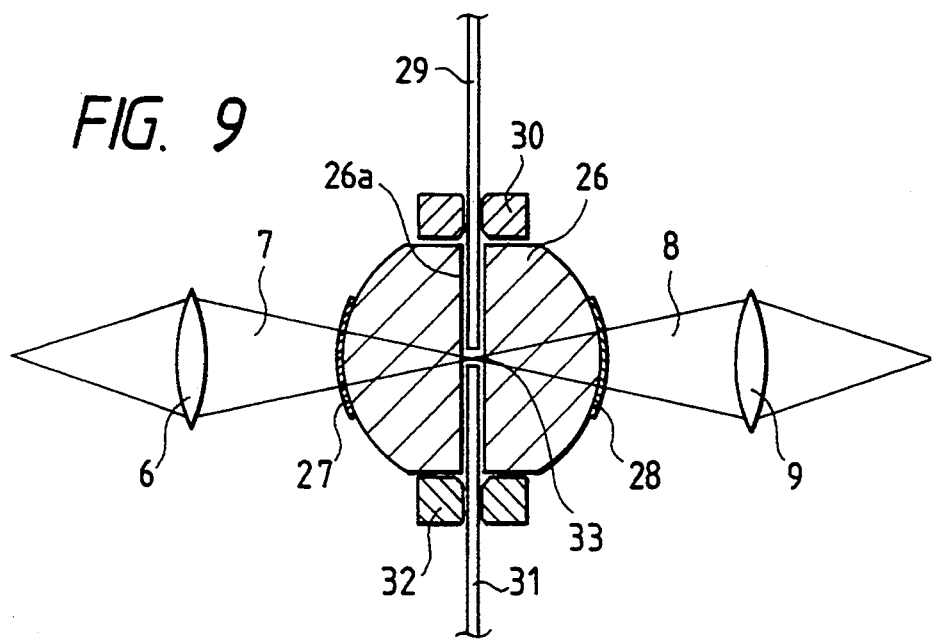

OPTICAL CELL AND OPTICAL DETECTION SYSTEMS LIGHT ABSORPTION

BACKGROUND OF THE INVENTION

The present invention relates to an optical cell or an optical detection system which are suitable for the optical detection of samples optically with high sensitivity. The present invention is also concerned with an optical cell or an optical detection system which are suitable for optical detection of samples such as protein, sugar and nucleic acid which have been isolated by a separating means such as, for example, a liquid chromatography system or a capillary electrophoresis system.

Electrophoresis is effective as means for separating and analyzing biological substances such as DNA, protein and sugar. Heretofore, agalose or polyacrylamide gel have mainly been used as mediums for electrophoresis. For examples, these gels have been used in the form of a slab gel between two glass plates or a capillary gel in the interior of capillary. Also, studies have been being made about a method of using a buffer alone without using gel as a medium for electrophoresis. At present, a capillary electrophoresis using a capillary of not larger than 100 $\mu$m in inside diameter is attracting attention of many concerns.

In electrophoresis using capillary such as, for example, capillary gel electrophoresis or capillary zone electrophoresis, since the capillary diameter is small, the surface area per volume of a migration medium is large and therefore the diffusion of joule heat is easy. Consequently, the rise of temperature is prevented even under the application of a high voltage and as a result it is possible to apply a higher voltage in comparison with the ordinary type of electrophoresis. That is, a high separating performance can be attained in a short time. Besides, because the capillary diameter is small, a small absolute amount of sample suffices, which is several ten nl (nanoliter) or so, and thus the capillary electrophoresis is suitable for microanalysis. For the detection of a sample isolated by electrophoresis there has been used an absorbance detected by a UV detector or a fluorescence intensity measured by a laser-excited fluorescence detection system. The capillary electrolysis is described, for example, in "Bunseki, No. 8" pp. 599–606 (1991) (published by the Japan Society for Analytical Chemistry).

Generally, in the electrophoresis using capillary, the concentration sensitivity [a detection limit (sensitivity) expressed in terms of a sample concentration] is insufficient, and fluorescence detection using laser beam as an excitation light has been studied as an attempt to attain a higher sensitivity. Studies have also been made about the method of measuring with a higher sensitivity an absorbance which is deficient in sensitivity. For example, FIG. 12 shows a conventional method which is described in "Analytical Chemistry, 63," pp. 1372–1376 (1991). In this conventional method, a silver reflection coating 102 and a protective coating 103 therefor are formed successively on an outer surface of a glass part 101 of capillary, and there are provided two very small windows for light incidence and exit, which are a window 105 of incident light and a window 106 of transmitted light and which are free of reflection coating. The windows 105 and 106 are formed in positions spaced from each other in the direction of capillary axis so that the incident light from the incident light window 105 may not directly go out straight from the transmitted light window 106. During measurement, a helium-neon laser beam 107 is made incident from the window 105 obliquely at a predetermined certain angle $\theta$ of incidence, then as shown in FIG. 12, it is reflected multi-reflectionwise in the capillary interior by the reflection coating and is allowed to pass a sample solution part 104 in a large number of times. Thus, the light path length is made longer to increase the amount of light absorbed. Thereafter, the output laser beam from the transmitted light window 106 is sensed to determine an absorbance.

SUMMARY OF THE INVENTION

The capillary electrophoresis referred to above is characterized in that an absolute amount of sample to be analyzed is small and that it is possible to detect a very small amount of sample. In general, however, since the capillary itself serves as an optical cell in optical detection, the light path length is not larger than the inside diameter of capillary and the detection sensitivity of concentration is not always good, so a detection method of higher sensitivity has been desired. As known well, absorbance (A) is calculated as A=$\epsilon$CL using a molar extinction coefficient ($\epsilon$), a sample concentration (C) and a light path length (L), and thus the sensitivity is proportional to the light path length. In the case of using capillary, the light path length is about 25 to 100 $\mu$m. It follows that the sensitivity is deteriorated 1/100 or so in comparison with the ordinary case (light path length of an optical cell: about 2 to 10 mm).

In the conventional example described in the foregoing "Analytical Chemistry, 63," pp. 1372–1376 (1991), incident light is allowed to pass through sample in a large number of times by multi-reflection to enlarge the light path length effectively, thereby improving the sensitivity. To this end, a reflection coating must be formed on capillary and thus a complicated operations have been required. More particularly, such processings as peeling a polyimide polymer, forming a reflection coating, and accurately forming the reflection coating-free portions for incident light and output light, namely, the incident light window 105 and the transmitted light window 106, must be done for each capillary used in measurement. These processings have been complicated (FIG. 12). In measurement, moreover, a measured value varies depending on an aligned state of laser beam with respect to the incident light window of capillary and the setting of an incidence angle, so it has been difficult to make adjustment for the alignment. Further, in the above conventional example, all the other portions than the incident light window and transmitted light window are covered with reflection coating and it is difficult to form a fluorescence receiving window. Thus, the conventional method in question has been unsuitable for fluorescence detection.

It is an object of the present invention to provide an optical cell and an optical detection system which are simple in structure, have a light path length equal to that of capillary and are capable of detecting a sample with high sensitivity.

It is another object of the present invention to provide an optical cell and an optical detection system which are for detection, optically with high sensitivity, a sample isolated by a liquid chromatography system or a capillary electrophoresis system, as well as a sample separation and detection system using them.

According to the present invention, for achieving the above-mentioned objects, in an optical cell having a sample solution in the interior thereof and functioning to detect a sample optically using incident light, the surface of the optical cell at least on an exit side of the incident light is formed as a half transmitting mirror. Further, in an optical detection system for optically detecting a sample contained in an optical cell, a half transmitting mirror is provided outside the surface of the optical cell at least on an exit side of incident light, and the surface of the optical cell on which light is incident is made approximately parallel with the exit surface.

Further, the following constructions are provided according to the present invention. Light incidence and exit surfaces of an optical cell are each in the shape of a curved surface, and a half transmitting mirror is not provided in the incident position of incident light. There is used a cylindrical optical cell, and a 100% reflection film is formed on the cylindrical surface except light incidence and exit surface portions, with a half transmitting mirror not provided in the incident position of incident light.

The reflectance of a half transmitting mirror corresponding to the incidence surface should be not greater than that of a half transmitting mirror corresponding to the exit surface.

In a sample separation and detection system including a sample solution separating means and an optical detector portion for detecting the separated sample optically, the foregoing optical cell or optical detection system is used as the optical detector portion. More specifically, a sample is separated by a liquid chromatography system or an electrophoresis system and is detected by the foregoing optical cell or optical detection system.

Moreover, in a sample separation and detection system using a sheath flow cell provided with a sheath solution inlet and a sample solution inlet, a 100% reflection film is formed on part in the longitudinal direction of the cylindrical surface, except light incidence and exit surface portions, of the sheath flow cell which is cylindrical and serves as a sample solution flow path, and light is made incident from the incident position of incident light where a half transmitting mirror is not provided, to detect the sample optically.

In an optical cell which holds a sample solution in the interior thereof and which detects the sample optically by irradiating light to the sample, the surface of the optical cell at least on an exit side of incident light is formed as a half transmitting mirror by forming thereon a reflection coating having a reflectance smaller than 1 (i.e. 100%), whereby the incident light which has entered the optical cell is partially reflected by the half transmitting mirror portion of the cell, while the remaining portion of the light passes through the mirror portion. The reflected light further repeats this process in a multi-reflection manner and as a result, although the details will be described later, an absorbance obtained from both an output light intensity in the presence of a sample and that in the absence of a sample increases in an effective manner, thus giving rise to an effect equal to that of an increase in the light path length (or an increase of the sample concentration, whereby it is made possible to effect the detection of sample in a higher concentration. Further, an optical axis of incident light and that of output light are substantially the same as in the ordinary measurement made in the absence of a half transmitting mirror, and thus the adjustment of optical axis can be done easily.

At least outside the light exit surface of the optical cell portion there may be provided a half transmitting mirror perpendicular to a light radiation axis, whereby there also can be obtained the same effect as above.

The half transmitting mirror can be fabricated by a known method such as, for example, vapor deposition of a dielectric multilayer coating film to a suitable thickness. Although the details will be explained later, by setting the light reflectance of the half transmitting mirror at a value larger than 0 (i.e. 0%), the light path length can basically be made longer in an effective manner, whereby it is made possible to effect the detection of sample in a higher sensitivity.

On the other hand, the other optical cell surface than the light incidence and exit side surface thereof may be made transparent if only the half transmitting mirror is positioned on or outside the light incidence and exit side optical cell surface. The use of this transparent surface permits fluorescence detection perpendicularly to the axis of incident light. When the sample concentration is low, the total intensity of light irradiating a sample by multi-reflection can be made almost equal to the intensity detected in the absence of the half transmitting mirror, so the sensitivity in fluorescence detection will not be deteriorated. Besides, when the reflectance of the half transmitting mirror corresponding to the incidence surface is lower than that corresponding to the exit surface, the total intensity of light irradiating a sample becomes larger in comparison with the intensity detected in the absence of the half transmitting mirror, and the fluorescence intensity increases, so that it is also possible to improve the detection sensitivity in fluorescence detection.

Further, a sample which has been separated by a liquid chromatography system or an electrophoresis system can be detected in high sensitivity using the foregoing optical cell or optical detection system as an optical detector portion of such sample separation and detection system.

BRIEF DESCRIPTION OF THE DRAWINGS

FIG. 8 is a sectional view showing a sample detecting portion of an electrophoresis system provided with an optical detection system which comprises an optical cell having parallel half transmitting mirrors according to a fish embodiment of the present invention;

FIG. 9 is a sectional view showing a sample detecting portion of an electrophoresis system provided with an optical detection system which comprises an optical cell having half transmitting spherical mirrors according to a sixth embodiment of the present invention;

DESCRIPTION OF THE PREFERRED EMBODIMENTS

Embodiments of the present invention will be described in detail hereinunder with reference to FIGS. 1 to 11.

First Embodiment

Figure 1:
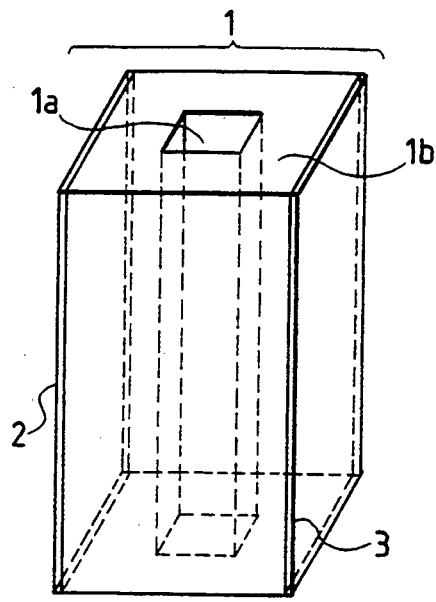
FIG. 1 is a perspective view of an optical cell having parallel half transmitting mirrors according to a first embodiment of the present invention.

FIG. 1 is a perspective view of an optical cell having parallel half transmitting mirrors, embodying the present invention. An optical cell 1 is composed of a fused-silica glass block 1b 3 mm square in external form by 10 mm in length having a sample solution flow path 1a which is formed along a central axis and which is 1 mm in light path width and length, and half transmitting mirrors 2 and 3. The sample solution flow path 1a has openings at its upper and lower ends. Thus, the optical cell 1 is a so-called flow cell type. The half transmitting mirrors 2 and 3, which are formed on a pair of opposed faces of the optical cell 1, have a reflectance smaller than 1 (100%), say, 0.99 (99%). They are formed in a conventional manner, that is, by vapor-depositing a dielectric multilayer coating film on the said faces of the fused-silica glass block 1b. In the case of detecting an absorbance using the optical cell 1, incident light is transformed into parallel beams, which are allowed to enter the optical cell while adjustment is made to let the parallel beams pass perpendicularly through the surface of the half transmitting mirror 2 and that of the half transmitting mirror 3 located on the opposite side with respect to the sample solution flow path 1a.

Figure 2:
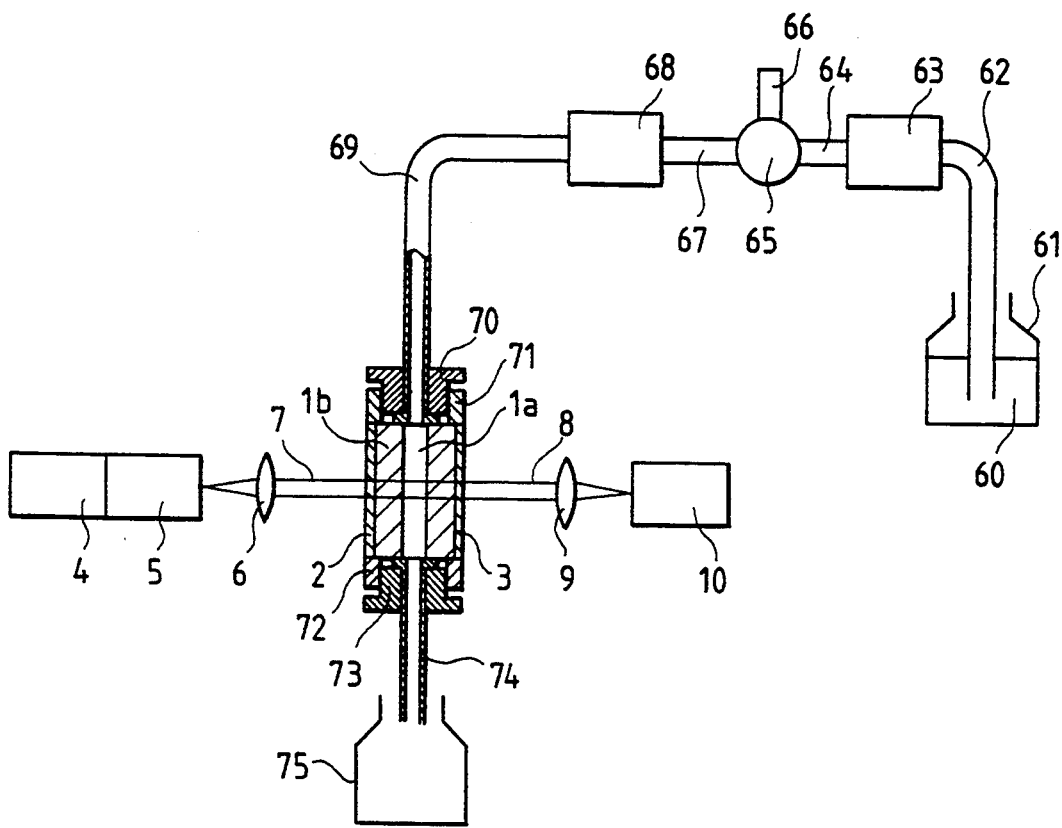
FIG. 2 is a basic construction diagram of a sample separation and detection system provided with the optical cell having parallel half transmitting mirrors in the first embodiment.

FIG. 2 is a basic construction diagram of a sample separation and detection system using the above optical cell. This figure illustrates a system construction for separating a sample by means of a liquid chromatography system and detecting the separated sample in terms of absorbance using the above optical cell. The construction for separating a sample will now be described. An elution solution 60 in an elution solution reservoir 61 is delivered through an injection valve 65 and a column 68 to the optical cell 1 and is discharged to a waste bottle 75, by means of a pump 63. These components are connected using fluorine-contained polymer tubes 62, 64, 67, 69 and 74 to form a flow path. The structure near the optical cell 1 is such that the optical cell is fixed using parts 71 and 72 for fixing optical cell 1, and the fluorine-contained polymer tubes 69 and 74 are brought into close contact with the optical cell by means of screws 70 and 73 to form a flow path. Connection to the pump 63 and column 68 is also effected using fluorine-contained polymer tubes. A sample solution to be detected is poured in a predetermined amount from a sample solution inlet 66 of the injection valve 65 (e.g. Model 7125 Injector, a product of Reodyne Inc.) and is sent to the column 68 by change-over of the valve. The sample solution is separated by the column, forms a specific band and passes through the fluorine-contained polymer tube 69 and optical cell 1. During passage through the optical cell, the sample is detected optically.

The following description is now provided about an optical detector portion. Light from a light source 4, e.g. Xenon lamp, is split into monochromatic light by means of a spectroscope 5. Further, the monochromatic light is transformed into a collimated light by means of a lens 6, which light is used as an incident light 7 for the detection of absorbance. The incident light 7 is allowed to incident on the half transmitting mirror 2 of the optical cell 1 perpendicularly thereto. Part of the incident light 7 is directed into the optical cell 1 by the mirror 2 and passes through the sample solution flowing through the sample solution flow path 1a. The thus-transmitted light is reflected and transmitted at the half transmitting mirror 3. The reflected light again passes through the sample solution and is then reflected and transmitted at the half transmitting mirror 2. The incident light repeats these processes and finally the sum total of light passing through the half transmitting mirror 3 corresponds to a transmitted light 8. The transmitted light 8 is condensed by a lens 9 and detected by a photomultiplier 10. Though not shown in the figure, the output of the photomultiplier 10 is amplified by an amplifier and processed by a data processor to calculate an absorbance.

In detecting an absorbance, it is necessary to detect a transmitted light in the absence of a sample, as a reference light, in addition to a sample transmitted light which is a signal light. In FIG. 2, since only detector is used, the intensity of a transmitted light through a solution not containing a sample is measured in advance and an absorbance is calculated on the basis of the measured value. In connection with FIG. 2, there may be adopted a system construction in which incident light is divided in two, then one is allowed to pass through a sample solution and detected, while the other is allowed to pass through a solution not containing a sample and detected. In this case, in addition to the components shown in FIG. 2, for dividing the incident light in two there are disposed, according to the conventional method, a half mirror (half transmitting mirror) having a transmittance and a reflectance of both 0.5 (i.e. 50%), as well as another set of optical cell, lens and photomultiplier.

In the system of this embodiment, the incident light 7 and the transmitted light 8 are substantially coaxial optically, so the system can be constructed easily. Moreover, since the incident light 7 and transmitted light 8 are optically coaxial with the conventional system, the system of this embodiment can be constructed by only replacing the optical cell portion of the conventional system with the optical cell portion according to this embodiment. Further, an optical adjustment of optical axis is easy because the transmitted light is received through a half transmitting mirror.

Using various concentrations of acridine orange solutions as sample solutions, absorbances for 470 nm wavelength light were detected to check the performance of the optical detector portion of the sample separation and detection system having the above construction. As a result, it turned out that the sensitivity could be improved ten times or more as high as that obtained in the absence of a half transmitting mirror. Thus, according to the sample separation and detection system, i.e. liquid chromatography system, having the construction of this embodiment, it is possible to effect a sample detection with a sensitivity about ten times as high as the conventional sensitivity. The principle of the improvement in detection sensitivity attained by the provision of half transmitting mirrors will be described below.

Figure 3:
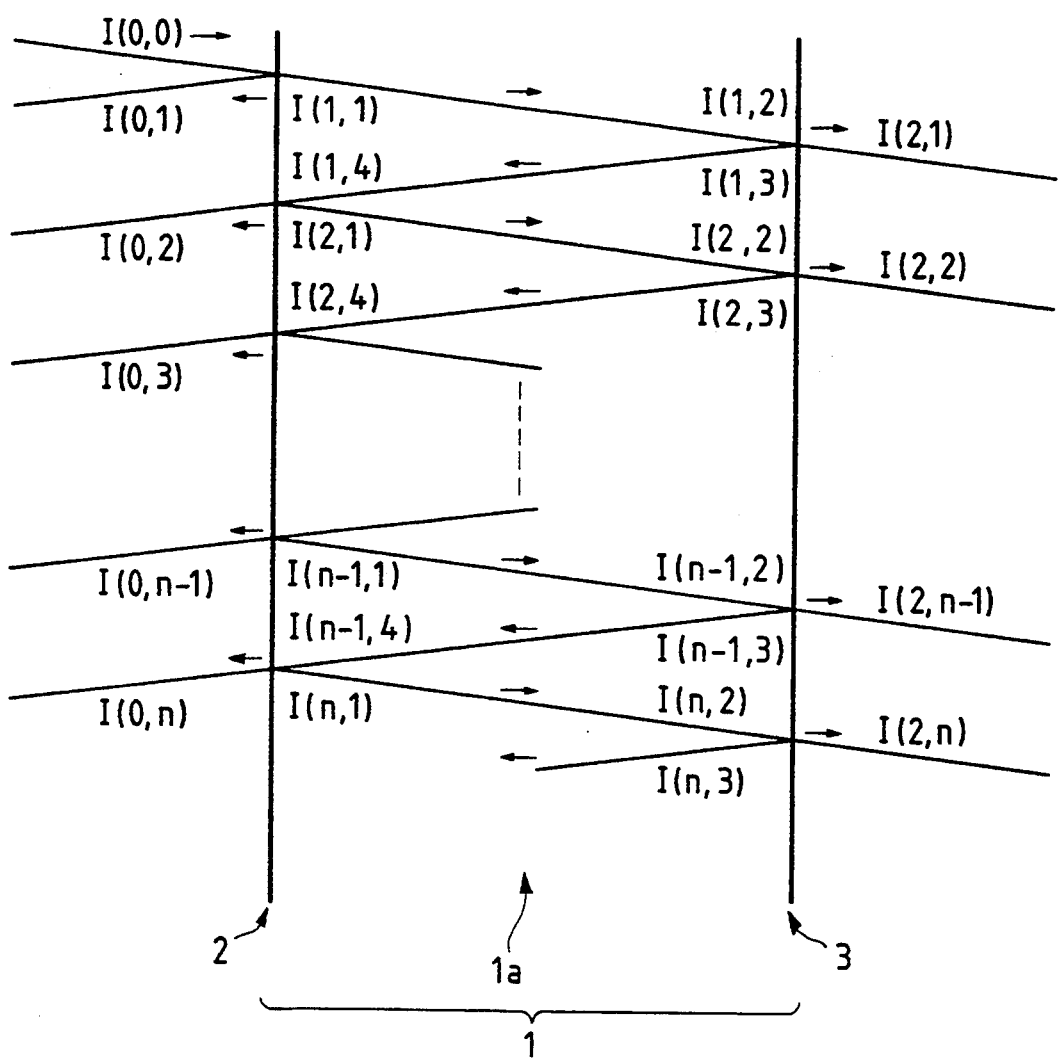
FIG. 3 is a diagram explanatory of optical paths of incident light, reflected light and transmitted light at the optical cell portion in the first embodiment.

FIG. 3 is a diagram explanatory of optical paths of incident light, reflected light and transmitted light at the portion of the optical cell 1. The optical paths are originally all coaxial, but in FIG. 3 they are shown obliquely for explaining the state of reflection and that of transmission. In the same figure, I(n,m) (n,m=0, 1, 2, . . . ) indicates each light intensity. I(0,0) indicates the intensity of the incident light 7. I(0,m) indicates a component of light which is incident at $m^{th}$ time on the half transmitting mirror 2 in the course of reflection and transmission, the said component advancing to the exterior of the optical cell. I(n,1) indicates a component of light which is incident at $n^{th}$ time on the half transmitting mirror 2, the said component advancing toward the inside of the optical cell. I(n,2) indicates a component after passing through a sample, with I(n,1) used as incident light. I(n,3) indicates a component of I(n,2) which component is reflected by the half transmitting mirror 3. I(n,4) represents a component after passing through a sample, with I(n,3) used as incident light. I(2,n) represents a component of I(n,2) which component passes through the half transmitting mirror 3.

That is, in the half transmitting mirror 2, there exist the following relations:

$$I(0,0) = (0,1) + I(1,1)$$

$$I(n-1,4) = I(n,1) + I(0,n)$$

In the half transmitting mirror 3, the following relation is established:

$$I(n,2) = I(n,3) + I(2,n)$$

It is here assumed that the reflectance of the half transmitting mirror 2 is $r_1$ ($0 \leq r_1 < 1$), that of the half transmitting mirror 3 is $r_2$ ($0 \leq r_2 < 1$), and a molar extinction coefficient of a sample solution, concentration thereof and light path lengths defined by optical cell 1, respectively, are $\epsilon$, C and $L_0$. As known well, an absorbance $A_0$ in the ordinary measurement is expressed as $A_0 = \epsilon C L_0$, and if a transmittance based on absorption of a sample itself exclusive of the influence of a solvent, etc. is assumed to be $\epsilon$ ($0 \leq \epsilon \leq 1$), $A_0 = \log(1/\epsilon)$. As a result, the following sequence is obtained:

$$I(n-1,2) = I(n-1,1)\alpha \tag{1}$$

$$I(n-1,3) = I(n-1,2)r_2 \tag{2}$$

$$I(n-1,4) = I(n-1,3)\alpha \tag{3}$$

$$I(n,1) = I(n-1,4) r_1 \tag{4}$$

$$I(2,n-1) = I(n-1,2)(1-r_2) \tag{5}$$

An initial value is:

$$I(1,1) = I(0,0)(1-r_1) \tag{6}$$

It is assumed that absorption occurs due to only a sample to be detected and the reflection at the glass interface is negligible, or that the influence of reflection at the glass surface is included effectively in the reflectance of each half transmitting mirror. From the equations (1) to (6), I(n,1) is obtained as:

$$I(n,1) \; 32 \; I(0,0)(1 - r_1)(r_1 r_2 \alpha^2)^{n-1} \tag{7}$$

And the component which passes through the half transmitting mirror 3 is:

$$I(2,n) = I(0,0)\alpha(1 - r_1)(1 - r_2)(r_1 r_2 \alpha^2)^{n-1} \tag{8}$$

The intensity of the transmitted light 8, ( I ( out ) ), in FIG. 2 is the sum total of I(2,n) and is calculated as follows:

$$I(\text{out}) = \sum_{n=1}^{\infty} I(2,n) = \lim_{n \to \infty} \sum_{k=1}^{n} I(2,k)$$

$$= \frac{\alpha(1 - r_1)(1 - r_2)I(0,0)}{1 - r_1 r_2 \alpha^2} \tag{9}$$

Usually, for the measurement of absorbance and transmittance, both the intensity, I(s), of light which has passed through a sample and the intensity, I(r), of light which has passed through a solution not containing a sample, as reference, are measured and calculated, and the absorbance is given as log(I(r)/I(s)). The intensity I(s) is a value obtained when $1 > \alpha 0$ in I(out) of the equation (9), while the intensity I(r) is a value when $\alpha = 1$ therein. If the absorbance at this time is assumed to be $A_1$, then from the equation (9), $$A_1 = \log((1 - r_1 r_2 \alpha^2)/(\alpha(1 - r_1 r_2))) \tag{10}$$

Upon comparison thereof with the absorbance $A_0$ in the ordinary measurement not using a half transmitting mirror, the ratio (R) of the two is given as:

$$R = A_1/A_0 \tag{11}$$

$$= 1 + \log((1 - r_1 r_2 \alpha^2)/(1 - r_1 r_2))/\log(1/\alpha)$$

As long as $\alpha \leq 1$, $R \leq 1$, and particularly when $(1 >) r_1 r_2 > 0$, $R > 1$. If an apparent light path length in the presence of a half transmitting mirror is assumed to be $L_1$, $A_1 = \epsilon C L_1$, and since $A_0 = \epsilon C L_0$, $L_1 = R L_0$. This is equivalent to the light path becoming R times longer, and even in the case of a sample of a lower concentration, the apparent light path length becomes longer, whereby it is made possible to detect the sample in a higher sensitivity.

From the equation (11), when $r_1 r_2 = 0$, $R = 1$ and it is impossible to improve the sensitivity. For improving the sensitivity, it is necessary to satisfy the condition of $r_1 > 0$ and $r_2 > 0$. In other words, the sensitivity can be improved by using the half transmitting mirrors 2 and 3 which are not zero in reflectance. For example, when $A_0 = 0.001$, if $r_1 = r_2 = 0.6$, then $A_1 = 0.0021$ and thus the absorbance approximately doubles. Further, if $r_1 = r_2 = 0.9$, then $A_1 = 0.090$ and thus the absorbance increases to about 90 times. That is, even in the case of a sample which usually affords only an absorbance of the noise level or lower, it becomes possible to fully detect the sample with high sensitivity. Although these values are the results of theoretical calculations, a tenfold or more increase in absorbance could be confirmed as a result of actual measurements.

The transmitted light intensity I(out) detected by the optical detector after passing through a sample is lower than that in the absence of a half transmitting mirror, i.e. $\alpha I(0,0)$. In other words, since the transmitted light is weaker than that in the ordinary case, it is necessary to use a light detecting means sensitive enough to compensate for this point. For example, therefore, a photomultiplier 10 of high sensitivity is used as the optical detector, or a bandpass interference filter is used as the spectroscope for enhancing the intensity of the incident light 7, or a laser beam is used. By using such means it is made possible to detect transmitted light with a high accuracy and detect an absorbance in high sensitivity.

According to this embodiment, since a pair of opposed faces of the optical cell are formed as half transmitting mirrors, there occurs multi-reflection of incident light between the half transmitting mirrors and the light path length increases effectively, so that a sample absorbance can be detected in high sensitivity and it is possible to detect a sample in a sensitivity ten times or more as high as the conventional sensitivity. Consequently, particularly in the case of using an optical cell having a short light path length or in the case where the sample concentration is low, it is possible to measure absorbance in high sensitivity. An optical adjustment for an optical axis, etc. can also be done easily, thus permitting easy fabrication of the system.

Although a flow cell type optical cell has been described above, this embodiment is also applicable to an ordinary type of an optical cell having a closed bottom.

If the sum total of light which irradiates the sample in the optical cell 1 repeatedly due to reflection, etc. at the half transmitting mirrors is assumed to be I(all), then:

$$I(\text{all}) = \sum_{n=1}^{\infty} (I(n,1) + I(n+3)) \qquad (12)$$

$$= \frac{\alpha(1 - r_1)(1 + r_2\alpha) I(0,0)}{1 - r_1 r_2 \alpha^2}$$

Consideration will here be given about the case where the sample concentration is low. For example, when $\alpha \approx 1$, if $r_2 \geq r_1$, then $I(\text{all}) \geq I(0,0)$. Thus, even in the presence of half transmitting mirrors, a larger amount of light than that of the original incident light can be radiated to the sample. That is, also in the case of fluorescence detection, by employing an optical cell in which the reflectance of half mirror is represented by $r_2 \geq r_1$, it is possible to emit fluorescence to an extent equal to or higher than that in the conventional method not using a half transmitting mirror and it becomes possible to effect fluorescence detection in a sensitivity almost equal to or higher than that in such conventional method. In this case, for measuring the intensity of fluorescence, fluorescence is received from a direction perpendicular to the incident direction of the incident light 7, and as a matter of course, a half transmitting mirror is not provided on the optical cell face located in the fluorescence receiving direction. Thus, the optical cell of this embodiment is employable not only for the detection of absorbance but also for the detection of fluorescence.

As to absorbance, the degree of its increase is determined by the product $r_1 r_2$ according to equation (10), not depending on the value of each of $r_1$ and $r_2$. Therefore, by using an optical cell which satisfies $r_2 \geq r_1$ while maintaining the product value of $r_1$ and $r_2$ in absorbance detection, it becomes possible to effect the detection of absorbance and that of fluorescence effectively using the same cell. Besides, an optical system required therefor can also be fabricated easily.

Figure 4:
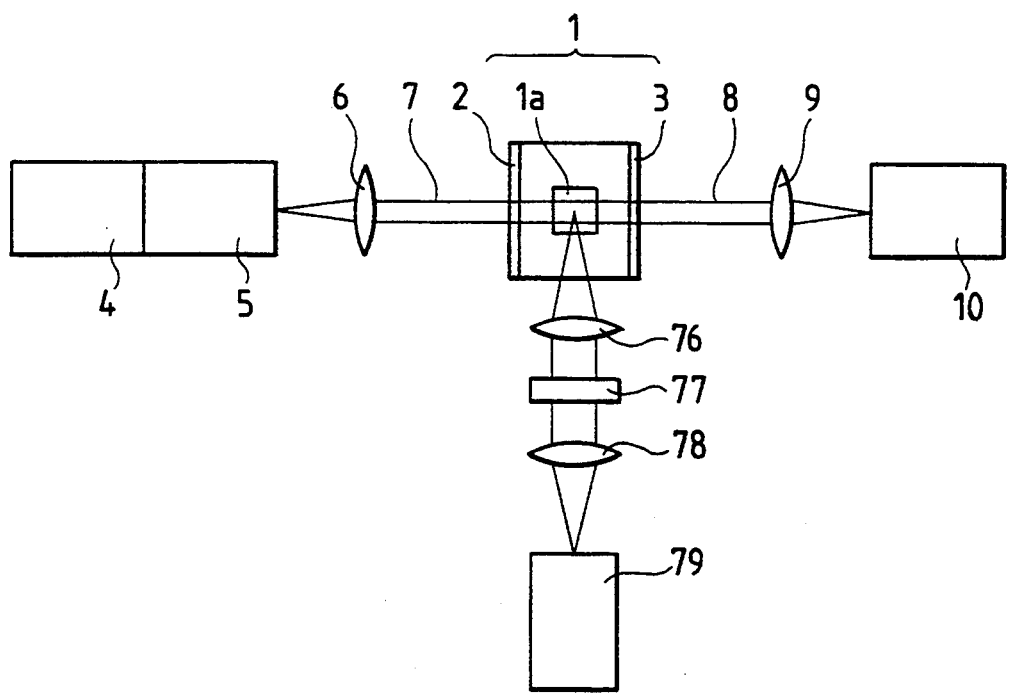
FIG. 4 is a basic construction diagram of an absorbance and fluorescence simultaneous detection system provided with the optical cell having parallel half transmitting mirrors in the first embodiment.

FIG. 4 is a basic construction diagram of an absorbance/fluorescence simultaneous detection system comprising the above optical cell. In the same figure, the construction of an absorbance and fluorescence detecting portion is shown on a plane including an incident light axis and fluorescence detection axis. In the system illustrated therein, in addition to the components of the system shown in FIG. 2, there are further used a lens 76 for the condensing of light, a spectrofilter (or a spectroscope) 77, e.g. interference filter, a lens 78 and a photomultiplier 79, for detecting fluorescence emitted from the optical cell 1, from a direction perpendicular to the direction of the incident light 7. An amplifier and a data processor for processing the output of the photomultiplier, as well as a power source, are omitted in FIG. 4.

For example, if there is used an optical cell having a half transmitting mirror 2 whose reflectance $r_1$ is 0.99 (99%) and a half transmitting mirror 3 whose reflectance $r_2$ is 0.995 (99.5%), the absorbance detecting sensitivity is enhanced about ten times; besides, the amount of light for exciting a sample is about the same as that of the incident light, thereby permitting the sample to be excited to a satisfactory extent. Thus, it is possible to effect fluorescence detection of the sample in a sensitivity equal to that in the conventional method.

Generally, a sample concentration range capable of being determined by absorbance detection and that capable of being determined by fluorescence detection are different from each other, with the fluorescence detection range being on a lower concentration side. In this embodiment, in the case of using an acridine orange solution as sample, 0.1 μM or less to about 100 μM can be determined by absorbance detection, and 1 μM or less to about 0.1 nM can be determined by fluorescence detection. Thus, by performing both detections simultaneously, it is made possible to expand the determination range to a greater extent and detect from low to high concentration of sample solutions as they are. Consequently, the sample diluting operation and concentrating operation can be simplified.

Further, since one sample is detected using a single cell by two different methods which are an absorbance detecting method and a fluorescence detecting method, it is also possible to improve the detection accuracy.

According to this embodiment, half transmitting mirrors are provided on only the light incident surface and exit surface of an optical cell and their reflectances satisfy the relation of $r_2 \geqq r_1$, whereby the absorbance detection sensitivity can be enhanced and it is possible to effect the detection of fluorescence in a sensitivity equal to that in the conventional method.

Second Embodiment

Figure 5:
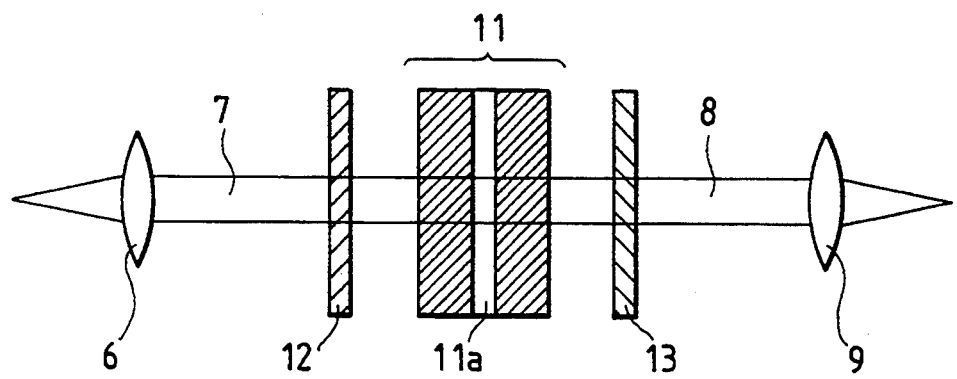
FIG. 5 is a sectional view showing the construction of an optical detection system, with half transmitting plane mirrors being separated from an optical cell, according to a second embodiment of the present invention.

Reference will now be made to another embodiment of the invention in which the construction of an optical cell portion used is different from that of the optical cell portion used in the first embodiment. FIG. 5 illustrates the construction of an optical detection system in which half transmitting plane mirrors are separated from an optical cell. More specifically, half transmitting mirrors 12 and 13 are disposed outside a light incidence surface and outside a light exit surface, respectively, of an optical cell made of fused-silica glass 3 mm square in external form and having a flow path of 1 mm in both light path width and length, the half transmitting mirrors 12 and 13 being disposed in parallel with the light incidence surface and exit surface, respectively. Light for detection is collimated by a lens 6, then is directed approximately perpendicularly to the surface of the half transmitting mirror 12. Transmitted light 8 after passing through the half transmitting mirror 13 is condensed by a lens 9 and detected in the same manner as in the first embodiment. The flow path 11a of the optical cell 11 is open at both upper and lower ends thereof. Tubes are combined therewith as in FIG. 2 for use as a flow cell. As to the sensitivity in the detection of absorbance and that in the detection of fluorescence, a higher sensitivity detection of a sample can be attained by absorbance detection as in the first embodiment. According to this embodiment, since half transmitting mirrors are disposed outside the optical cell, it is not necessary to process surfaces of the optical cell itself into half transmitting mirrors and hence the cost is so much reduced. Besides, since the half transmitting mirrors can be exchanged easily, it is possible to readily select a combination of half transmitting mirrors having desired reflectances, and optimum half transmitting mirrors can be used according to a sample to be detected. In this embodiment, because half transmitting mirrors are disposed exteriorly of the optical cell, there exists reflection at the interface between the optical cell and the air, but the reflectance of each half transmitting mirror is set in consideration of the influence of such reflection. Actually, however, since absorbance is calculated on the basis of the intensity of light passing through a liquid not containing a sample, the influence of the said reflection can be ignored and it is possible to effect a high sensitivity detection of a sample as in the first embodiment. In this embodiment, one of the half transmitting mirrors 12 and 13 may be provided on the light incidence surface of the optical cell, and also in this case there can be obtained the same effect as above.

Third Embodiment

Figure 6:
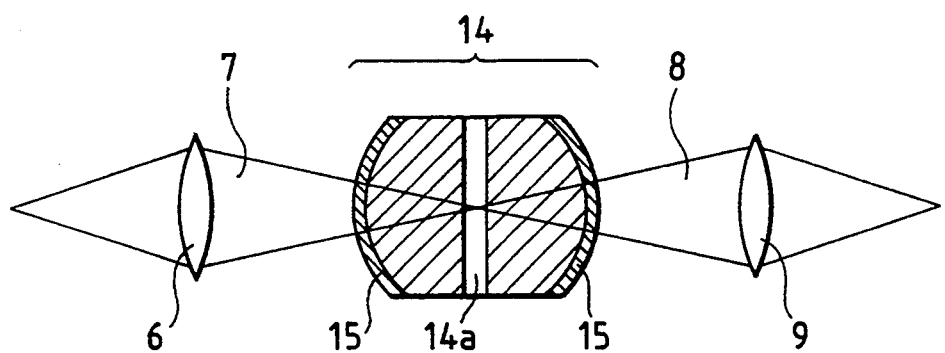
FIG. 6 is a sectional view showing the construction of an optical detection system comprising an optical cell having spherical half transmitting mirrors according to a third embodiment of the present invention.

A further embodiment having an optical cell portion different in structure from the above embodiments will now be described. FIG. 6 is a sectional view showing the construction of an optical detection system which comprises an optical cell having spherical half transmitting mirrors. In an optical cell 14 for the detection of light used in this embodiment, a flow path 14a 1 mm in light path width and length is formed in a central axis portion of a spherical fused-silica glass block having a radius of 3 mm, and the spherical portions of the upper and lower ends of the flow path 14a are cut off to provide surfaces perpendicular to the flow path. Further, reflection coatings having a reflectance of 0.95 (95%) are formed substantially over the whole surface of the spherical surface portions of the cell to form half transmitting mirrors 15. The sectional shape of the flow path 14a is not limited to the above rectangular shape, it may be circular. The fused-silica glass portion of the optical cell 14 need not be a single glass block. A plurality of fused-silica glass blocks may be fusion-bonded together to finally obtain a desired shape described above.

Light is made incident so as to be focused on the center of the spherical optical cell 14 by means of a lens 6. The incident light passes through the half transmitting mirror 15 located on the left-hand side, then passes through a sample solution which is flowing through the flow path 14a formed centrally of the optical cell, and reaches the half transmitting mirror 15 located on the opposite side. After going through the process of multi-reflection and -transmission, the light which has passed through the half transmitting mirror 15 on the opposite side is condensed by a lens 9 and detected. Thus, the incident light passes through the half transmitting mirrors at two portions of the optical cell 14. In this embodiment, the spherical surface portions of the cell are all formed as half transmitting mirrors of the same structure and hence the said two portions are half transmitting mirrors having the same reflectance.

In this case, absorbance increases and the absorbance detection sensitivity is improved as in the first embodiment, while the detection of fluorescence is unsuitable because fluorescence is intercepted by the half transmitting mirrors. Basically, it is sufficient for the half transmitting mirrors to be present at the above two portions through which the incident light passes, so the half transmitting mirrors may be formed at such portions alone. In this case, emitted fluorescence can be condensed and detected through a portion free of a half transmitting mirror, and this is suitable for the detection of fluorescence. In this embodiment, the position of a sample to be irradiated is at the center of the sphere, and the half transmitting mirrors are located on the surfaces of the sphere. That is, the light which has passed through the central sample position in the sphere is reflected by the opposite-side half transmitting mirror and returns to the sample position. Thus, the light passes through the same optical path multi-reflectionwise. Consequently, like the first embodiment, the sensitivity of absorbance or of fluorescence can be detected and it is possible to enhance the absorbance and detect the sample in high sensitivity.

According to this embodiment, moreover, since the incident light can irradiate the sample in a condensed state, the volume of the sample at the irradiated portion may be small and therefore it is possible to make the detection of absorbance in a finer region. Consequently, in the case where a sample flows in a separated, band-like form by liquid chromatography or electrophoresis, it is possible to detect the sample in high sensitivity with a high separating ability.

Further, according to this embodiment, since the incident light can irradiate the sample in a condensed state, the light intensity density of the sample irradiated portion becomes high, so that the intensity of emitted fluorescence can be detected with a higher accuracy and the fluorescence detection accuracy becomes higher.

Fourth Embodiment

Figure 7:
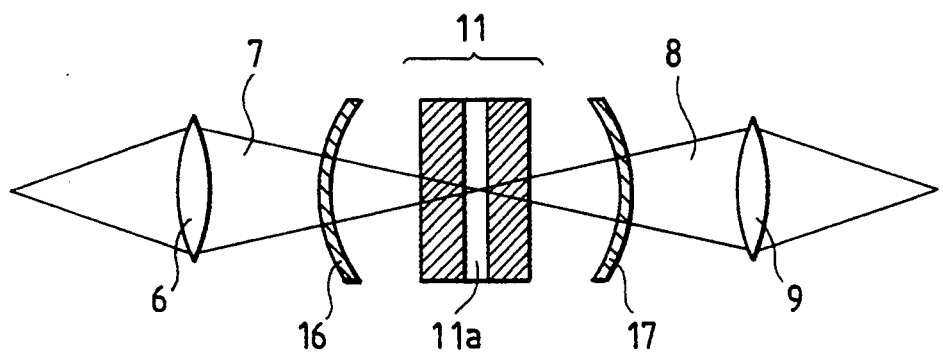
FIG. 7 is a sectional view showing the construction of an optical detection system, with half transmitting concave mirrors being separated from an optical cell, according to a fourth embodiment of the present invention.

A further embodiment having an optical cell portion different in structure from the previous embodiments will now be described. FIG. 7 is a sectional view showing the construction of an optical detection system in which half transmitting concave mirrors are separated from an optical cell. As an optical cell for the detection of light there is used the optical cell 11 described previously in the second embodiment. Half transmitting concave mirrors 16 and 17 are used in this embodiment in place of the half transmitting mirrors 12 and 13 used in the second embodiment illustrated in FIG. 5. As shown in FIG. 7, both concave surfaces of the half transmitting concave mirrors 16 and 17 face the optical cell 11, and both mirrors are disposed so that the respective concave surfaces are positionally coincident in the center of curvature. The optical cell 11 is fixed and held in such a manner that the center of its flow path 11a coincides with such center position of curvature. In this case, since light passes obliquely through the fused-silica glass block of the optical cell 11, the half transmitting mirrors 16 and 17 become slightly longer effectively in the radius of curvature of each concave surface due to refraction, so it is necessary that the half transmitting mirrors 16 and 17 be disposed in this consideration.

Light is made incident so as to be focused on the above center position of curvature by means of a lens 6. The incident light passes through the half transmitting concave mirror 16, enters the optical cell 11, passes through a sample solution flowing through the flow path 11a, and reaches the half transmitting concave mirror 17 located on the opposite side. After going through the process of reflection and transmission, the light which has passed through the half transmitting concave mirror 17 is condensed by a lens 9 and detected.

According to this embodiment, like the third embodiment, light passes multi-reflectionwise through the same optical path between the half transmitting mirrors 16 and 17. Consequently, as explained previously in the first embodiment, it is possible to increase the absorbance, etc., thus permitting the detection of a sample in a higher sensitivity.

According to this embodiment, there can be obtained about the same effect as in the third embodiment. Besides, since there is not used a spherical optical cell, it is not necessary to provide half transmitting mirrors on cell surfaces, thus resulting in that the optical cell used is less expensive. Further, like the second embodiment, it is possible to easily select half transmitting mirrors having desired values of reflectance.

Fifth Embodiment

The following description is now provided about a still further embodiment having an optical cell portion different in structure from the previous embodiments. FIG. 8 is a sectional view of a sample detecting portion of an electrophoresis system provided with an optical detection system which comprises an optical cell having parallel half transmitting mirrors. The optical detection system according to this embodiment is particularly suitable to an optical detector portion for capillary electrophoresis. An optical cell 18 is 3 mm square in external form, having a height of 20 mm, and along its central axis is formed a flow path 18a of a rectangular section, having 300 μm in both light path width and length. A pair of opposed surfaces of the optical cell 18 constitute half transmitting mirrors 19 and 20, which are formed by vapor deposition of a dielectric multilayer coating film on each of those surfaces. Adjustment has been made to give a reflectance of 0.99 (99%) with respect to both mirrors 19 and 20.

In capillary electrophoresis, the separation of a sample is performed using capillary. More specifically, there is used a fused-silica capillary 21 having an inside diameter of 100 μm, an outside diameter of 200 μm and a length of 40 cm, with 5% polyacrylamide gel incorporated in the interior thereof. A solution containing a mixture of plural samples is subjected to electrophoresis using the capillary, whereby the samples are separated for each molecular weight. The detection of sample is performed within the optical cell 18. First, the capillary 21 for electrophoresis charged with the polyacrylamide gel is inserted into the flow path 18a of the optical cell 18 and fixed with a binding tool. There also is provided another capillary 23. The capillary 23 is 5 cm long shorter than the capillary 21, and the interior thereof is charged with polyacrylamide gel. The capillary 23 is inserted into the flow path 18a of the optical cell 18 from the side opposite to the capillary 21 and then fixed with a binding tool 24. The capillaries 21 and 23 are adjusted by the binding tools 22 and 24 to maintain a predetermined certain gap (end-to-end distance of both capillaries) 25 in the flow path 18a. It is preferable that the gap 25 be short, not longer than about 1 mm. A buffer (tris-borate buffer) for migration is poured into the flow path 18a to fill the gap 25 and the spaces between the capillaries 21, 23 and the flow path 18a with the buffer. In a conventional manner (by the application of voltage in this embodiment), a sample is introduced into the capillary 21 from an end 21a of the capillary and a voltage is applied between the capillary end 21a and a capillary end 23a, so that the sample migrates from the capillary 21 to the capillary 23 through the gap 25. In the gap 25 the sample is detected optically. In the gap 25, since neither gel nor capillary is present, the scattering of light is difficult to occur and multi-reflection can be done effectively by the half transmitting mirrors 19 and 20.

Light for detection is made into a collimated light not larger in diameter than the length of the gap 25 by means of a lens 6, then the collimated light is made incident on the half transmitting mirror 19 of the optical cell 18 to irradiate the gap 25. The light which has passed through the gap 25 reaches the half transmitting mirror 20 positioned on the opposite side. After multi-reflection and transmission between the half transmitting mirrors 19 and 20, the light passing through the mirror 20 is condensed by a lens 9 and detected. Sensitivity, etc. are the same as the results obtained in the first embodiment; that is, a fine absorbance can be increased and it is possible to detect a sample of low concentration in high sensitivity. Also by fluorescence detection it is possible to detect a sample in a sensitivity equal to or higher than that in the conventional method.

According to this embodiment, a sample which is separated and allowed to migrate by electrophoresis can be detected in high sensitivity.

Although in this embodiment the capillary interior is filled with polyacrylamide gel, the present invention is also applicable to an electrophoresis wherein the capillary interior is filled with another kind of gel or an electrophoresis not using gel.

Sixth Embodiment

The following description is now provided about a still further embodiment having an optical cell different in structure from the previous embodiments. FIG. 9 is a sectional view of a sample detecting portion of an electrophoresis system provided with an optical detection system which comprises an optical cell having half transmitting spherical mirrors. This embodiment, like the fifth embodiment, relates to an optical detection system suitable to an optical detector portion for capillary electrophoresis. A basic construction thereof is the same as that of the fifth embodiment shown in FIG. 8. This optical detection system comprises an optical cell 26 having a flow path 26a and half transmitting mirrors 27 and 28, a capillary 29, a binding tool 30, a gap 33 and lenses 6 and 9.

The optical cell 26 has almost the same structure as that in the third embodiment shown in FIG. 6. The flow path 26a, which is 300 μm in both light path width and length, is formed along a central axis of a spherical fused-silica glass block having a radius of 3 mm, and the upper and lower spherical end portions of the flow path 26a are cut off to form surfaces perpendicular to the flow path. Further, the half transmitting mirrors 27 and 28 are formed only in the portions of the spherical surface where incident light passes and the vicinity thereof. Adjustment is made so that the reflectance of the half transmitting mirror 27 and that of the half transmitting mirror 28 are each set at 0.95 (95%).

The capillaries 29 and 31, which are filled with polyacrylamide gel, are fixed to the cell with binding tools 30 and 32 to maintain the gap 33 at the length of 0.2 mm and in the central position of the cell. The interior of the flow path 26a including the gap 33 is filled with a tris buffer for electrophoresis to form a migration path extending from the capillary 29 to the capillary 31 through the gap 33.

Light for detection is made incident so as to be focused on the gap 33 by means of the lens 6. The light passes through the half transmitting mirror 27, then passes through a sample solution which is flowing through the gap 33 formed centrally of the optical cell, and reaches the half transmitting mirror 28 located on the opposite side. After multi-reflection and transmission between both half transmitting mirrors 27 and 28, the light passing through the mirror 28 is condensed by the lens 9 and detected.

According to this embodiment, like the third embodiment, since the incident light passes multi-reflectionwise through the same optical path in the optical cell, a small absorbance can be enhanced and detected.

According to this embodiment, moreover, the incident light is condensed into a fine spot, which irradiates the gap portion with a sample migrating therein, so that the detection area is small and it is possible to detect an absorbance in a smaller area and hence possible to detect a sample which is flowing after band-like separation by electrophoresis or the like, in high separating ability and high sensitivity.

Further, according to this embodiment, like the third embodiment, since the incident light can irradiate a sample in a condensed state, the light intensity density of the sample irradiated portion is high and also in fluorescence detection it is possible to detect the intensity of fluorescence with a high accuracy.

Seventh Embodiment

Figure 10A:
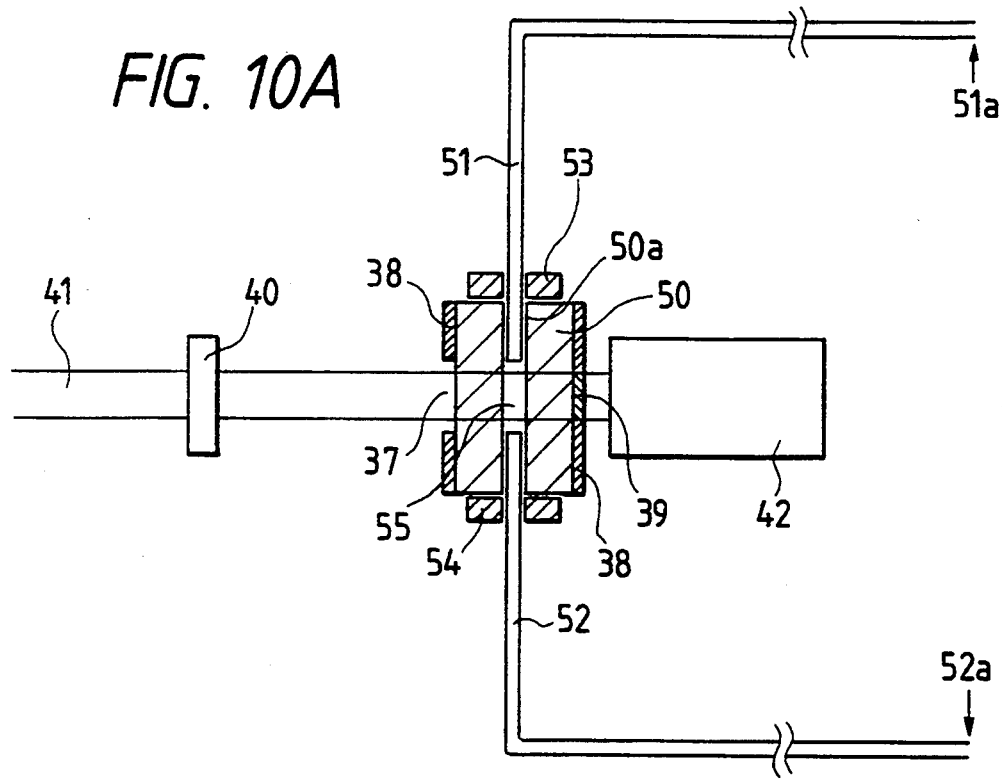
FIG. 10A is a sectional view including a flow axis and an incident light axis, and showing a sample detecting portion of an electrophoresis system provided with an optical detection system which comprises a cylindrical optical cell having a 100% reflection film over the greater part of its outer periphery according to a seventh embodiment of the present invention.
Figure 10B:
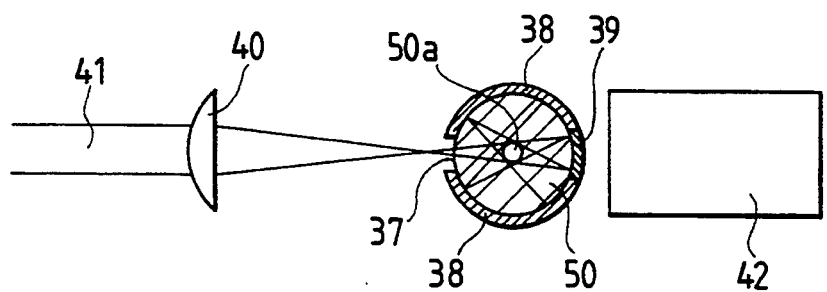
FIG. 10B is a sectional view of a plane perpendicular to a flow axis, including an incident light axis, and showing the sample detecting portion according to the seventh embodiment.

A still further embodiment of the present invention will now be described. FIG. 10 is a sectional view of a sample detecting portion of an electrophoresis system provided with an optical detection system which comprises a cylindrical optical cell having a 100% reflection film formed on the greater part of the outer periphery. In the same figure, FIG. 10A is a sectional view including a sample solution flow axis and an incident light axis, and FIG. 10B is a sectional view of a plane perpendicular to the flow axis, including the incident light axis. An optical cell 50 used in this embodiment is in the form of a cylinder having an has a flow path 50a on its central axis, the flow path 50a having an inside diameter of 300 μm. The greater part of the cylindrical surface of the optical cell 50 is covered with a 100% reflection film 38 having a reflectance of 1 (100%). In part of the cylindrical surface is formed a slit 37 having a width of 5 μm and a length of 1.5 mm which slit is elongated in the flow direction and in which neither a 100% reflection film nor a half transmitting mirror is present, while on the side substantially opposite to the slit 37 is formed a half transmitting mirror 39 (reflectance 0.99 (99%)) having a width of 100 μm and a length of 1.5 mm.

Fused-silica capillaries 51 and 52 having an inside diameter of 100 μm and an outside diameter of about 200 μm are fixed to the optical cell 50 by means of binding tools 53 and 54 as in the fifth embodiment. In the interior of the optical cell is formed a gap 55 which is 1.0 mm long. The interior of the capillary 51 and that of the capillary 52 are filled with 5% polyacrylamide gel. A buffer (tris-borate buffer) for migration is poured into the flow path 50a to fill the gap 55 and the spaces between the capillaries 51, 52 and the flow path 50a with the buffer. By a conventional method (by the application of voltage in this embodiment), a sample is introduced into the capillary 51 from an end 51a of the capillary and a voltage is applied between the capillary end 51a and an end 52a of the capillary 52, so that the sample migrates from the capillary 51 to the capillary 52 through the gap 55. In the portion of the gap 55 the sample is detected optically. In the gap 55, since neither gel nor capillary is present, the scattering of light is difficult to occur and multi-reflection is allowed to occur effectively by the half transmitting mirror 39 and the 100% reflection film 38.

Incident light 41, which is 0.8 mm in diameter, is condensed in one direction by a cylindrical lens 40 in conformity with the shape of the slit 37 and enters the cell in a direction connecting the slit 37 and the gap 55. By such an optical system it is made possible to introduce almost all of the incident light 41 into the optical cell where the cylindrical lens 40 has a focal length of about 6 mm, the spread in the sample position of the light which has entered the optical cell is approximately 100 μm, whereby a sample solution bundle passing through the gap 55, which is presumed to be about the same as the capillary inside diameter of 100 μm, can be irradiated efficiently. The light after passing through the sample is reflected by the 100% reflection film 38 or the half transmitting mirror 39. Then, the light thus reflected again passes through the sample solution and is reflected by the 100% reflection film 38 or the half transmitting mirror 39 in another position. Because the slit 37 is narrow, the probability of the thus-reflected light again returning to the position of the slit 37 is low, and it is presumed that almost all of the light rays are reflected by the curved surface on the incidence side. That is, there occurs a multi-reflection in a state in which the intensity of light entering the optical cell is almost equal to the incident light intensity in the system described in the first embodiment and the reflectance of the half transmitting mirror on the incidence side is approximately 1 (100%).

As a result of such multi-reflection, light passes through the half transmitting mirror 39 in a substantially extended state of the light path length. This transmitted light is then received by a photomultiplier 42 disposed in close contact with the optical cell and the intensity of the light is detected by a conventional method. For shielding the other light than the transmitted light it is necessary to provide a shield plate around the photomultiplier 42, which shield plate is not shown in the figure.

According to this embodiment it is possible to enhance a small absorbance and detect it in the same manner as in the first embodiment. Besides, unlike the first to the sixth embodiment, almost all of the incident light is conducted into the optical cell, so that the intensity of transmitted light becomes higher and hence the light intensity detection accuracy is improved, whereby the detection of absorbance can be done with a higher accuracy. According to this embodiment, therefore, a sample which is separated and allowed by migrate by capillary electrophoresis or the like can be detected in high sensitivity.

Although in this embodiment the capillary interior is filled with polyacrylamide gel, the invention is also applicable to the case where another kind of gel is charged into each capillary or the case where electrophoresis is performed without using gel.

Although the optical cell used in this embodiment is a cylindrical cell, it may be spherical as in the sixth embodiment. In the latter case, however, it is necessary to use an ordinary shape of lens in place of the cylindrical lens, and it is desirable that the shape of the slit and that of the half transmitting mirror be also made circular.

Although in this embodiment the slit 37 and the half transmitting mirror 39 are disposed in positions opposite to each other in a diametrical direction of the optical cell, no limitation is placed thereon. The half transmitting mirror 39 may be disposed in any position on the optical cell surface different from the slit position.

Further, according to this embodiment, almost all of the incident light irradiate the sample, which is also irradiated with reflected light at an intensity higher than that of the incident light to generate a high fluorescence intensity. In view of this point, the optical cell may be constructed in such a manner that a window free of a 100% reflection film is formed in part of a side face of the cell positioned in a direction generally perpendicular to the incident light direction, and the fluorescence intensity generated is taken out from the said window. This construction permits the reception of a higher fluorescence intensity and hence permits improvement of the sample detection sensitivity in fluorescence detection.

Eighth Embodiment

Figure 11A:
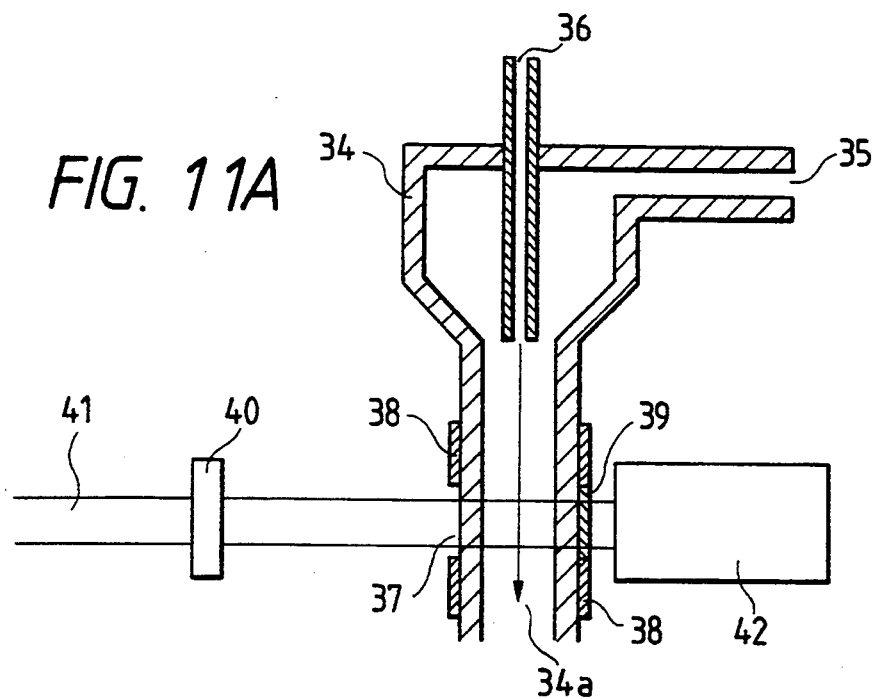
FIG. 11A is a sectional view including a flow axis and an incident light axis, and showing the construction of a sample separation and detection system for detecting a sample optically which system is provided with a cylindrical optical cell in part of a sheath flow cell according to an eighth embodiment of the present invention.
Figure 11B:
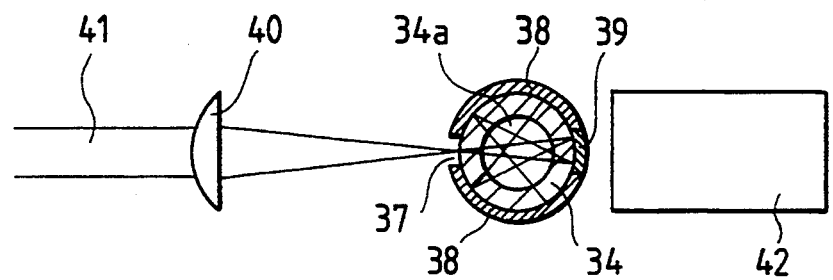
FIG. 11B is a sectional view of a plane perpendicular to a flow axis, including an incident light axis, and showing the construction of the sample separation and detection system according to the eighth embodiment.
Figure 12:
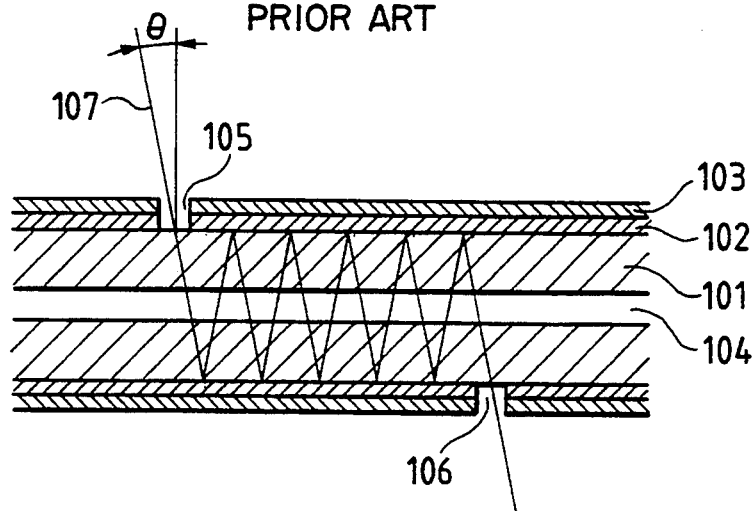
FIG. 12 is a sectional view of a conventional optical cell comprising a capillary and a reflection coating formed thereon.

A still further embodiment will now be described. FIG. 11 is a sectional view showing the construction of a sample separation and detection system for detecting a sample optically in which a cylindrical optical cell having a 100% reflection film on the greater part of its outer periphery as in the seventh embodiment is formed as part of a sheath flow cell. In this embodiment, the optical cell used in the seventh embodiment is formed as part of a sample flow path in a sheath flow cell 34. Thus, the optical cell constitutes a portion of the sheath flow cell 34. The sheath flow cell 34 has a sheath solution inlet 35 and a sample solution inlet 36. Like the seventh embodiment, the optical cell serving as a light detecting portion is in the shape of a cylinder having an outside diameter of 2 mm, and is provided on its central axis with a flow path 34a having an inside diameter of 400 $\mu$m. Further, a 100% reflection film 38, a slit 37 and a half transmitting mirror 39 which are the same as in the seventh embodiment are formed on the cylindrical surface of the optical cell.

A sample solution is separated in a column as in the ordinary liquid chromatography and the eluate obtained is poured as a sample solution into the sample solution inlet 36 of the sheath flow cell 34. As a sheath solution, degassed water is allowed to flow at a predetermined certain flow rate into the sheath solution inlet 35, and the eluate is allowed to flow in an enclosed state within the sheath solution through the optical cell which is a light detecting portion of the sheath flow cell 34. Like the seventh embodiment, an incident light 41 having a diameter of 0.8 mm is converged in conformity with the shape of the slit 37 by means of a cylindrical lens 40, and almost all the amount of the light is introduced into the cell. A suitable focal length of the cylindrical lens 40 is selected according to the diameter of the flowing sample solution and the width of the slit 37.

In a substantially extended state of the light path length due to multi-reflection, light passes through the half transmitting mirror 39. The transmitted light is then received by a photomultiplier 42 disposed in close contact with the optical cell which is a light detecting portion of the sheath flow cell 34, and the intensity of the light is detected by a conventional method. For shielding the other light than the transmitted light, it is necessary to provide a shield plate around the photomultiplier 42, which shield plate is not shown in the figure.

According to this embodiment, like the seventh embodiment, it is possible to enhance a fine absorbance and detect it.

Although in this embodiment the photomultiplier 42 is disposed in close contact with the optical cell, there may be adopted a construction wherein the transmitted light from the half transmitting mirror 39 is condensed and conducted to a photomultiplier using an ordinary type of lens.

According to the present invention, as set forth above, by forming at least a light exit side of an optical cell as a half transmitting mirror or by disposing a half transmitting mirror on the light exit side of the cell, it is possible to enhance absorbance in a simple and effective manner and hence possible to detect in high sensitivity a sample such as a sample solution of a low concentration or a sample solution present in a short optical path. Moreover, since incident light and output light can be made coaxial optically, it is possible to fabricate an optical detection system in a simple manner. Further, by coupling an optical cell or optical detection system according to the present invention with a separation means such as a liquid chromatograph or a capillary electrophoresis system, it is possible to effect a high sensitivity detection of a sample after separation by such separator means.

What is claimed is:

1. An optical cell for measuring light absorption by a sample solution in the cell comprising:
   a flow path having openings at first and second ends of the cell;
   a first half transmitting mirror being formed on an entire outside surface of a light incident side of the cell;
   a second half transmitting mirror being formed on an entire outside surface of a light output side of the cell;
   the first and second half transmitting mirrors being disposed so as to face each other; and
   an optical axis of an incident light to the cell and an optical axis of the output light from the cell being disposed on substantially a same axis.

2. An optical cell according to claim 1, wherein the light incident surface and the light output surface of the cell are flat surfaces disposed so as to be in parallel with one another.

3. An optical cell according to claim 1, wherein the first half transmitting mirror has a reflectance no greater than that of said second half transmitting mirror.

4. An optical cell for measuring a light absorption by a sample solution in the cell comprising:
   a flow path having openings at first and second ends;
   a first half transmitting mirror being formed on an entire outside surface at a light incident side of the cell;
   a second half transmitting mirror being formed on an entire outside surface at a light output side of the cell; and
   the first and second half transmitting mirrors being flat mirrors and disposed in parallel with one another.

5. An optical cell according to claim 4, wherein the optical cell has a substantially rectangular shape.

6. An optical detection system for light absorption comprising:
   separating means for separating a sample solution; and
   an optical cell for measuring light absorption by a sample solution in the cell and for optically detecting a separated sample, the cell having a flow path with openings at first and second ends, a first half transmitting mirror being formed on an entire outside surface of a light incident side of the cell, and a second half transmitting mirror being formed on an entire outside surface of a light output side of the cell, the first and second half transmitting mirrors being disposed so as to face each other, and an optical axis of an incident light to the cell and an optical axis of output light from the cell being disposed on substantially a same axis.

7. An optical detection system for light absorption according to claim 6, wherein the separating means includes one of a liquid chromatography system and a capillary electrophoresis system.

8. An optical detection system for light absorption according to claim 6, wherein the light incident surface and the light output surface are flat surfaces disposed so as to be in parallel to one another.

9. An optical detection system for light absorption comprising:
   separating means for separating the sample solution; and
   an optical cell for measuring light absorption by a sample solution in the cell and for optically detecting a separated sample, the cell having a flow path with openings at first and second ends, a first half transmitting mirror being formed on an entire outside surface of a light incident side of the cell, and a second half transmitting mirror being formed on an entire outside surface of a light output side of the cell, the first and second half transmitting mirrors being flat surfaces and disposed in parallel with one another, the first half transmitting mirror having a reflectance no greater than that of the second half transmitting mirror, and an optical axis of an incident light to the cell and an optical axis of output light from the cell being disposed on substantially a same axis.

10. An optical detection system for light absorption according to claim 9, wherein the separating means includes one of a light chromatography system and a capillary electrophoresis system.

11. An optical cell for measuring light absorption by a sample solution in the cell comprising:
    a flow path having openings at first and second ends and being formed in a central axial portion of a block of glass, the block being formed by cutting a spherical glass member so as to provide surfaces at the first and second ends;
    a half transmitting mirror being provided on the entire outside spherical surface of the block of glass; and
    an optical axis of incident light focusing on a center of the spherical glass of the cell and an optical axis of output light from the cell being disposed on substantially a same axis.

12. An optical detection system for light absorption comprising:
    separating means for separating a sample solution; and
    an optical cell for measuring light absorption by a sample solution in the cell and for optically detecting a separated sample, the cell having a flow path with openings at first and second ends and being formed in a central axial portion of a block of glass, the block being formed by cutting a spherical glass member so as to provide surfaces at the first and second ends, a half transmitting mirror being provided on an entire outside spherical surface of the block of glass, and an optical axis of incident light focusing on a center of the spherical glass of the cell and an optical axis of output light from the cell being disposed on substantially a same axis.

13. An optical detection system for light absorption according to claim 12, wherein the separating means includes one of a liquid chromatography system and a capillary electrophoresis system.

14. A cylindrical optical cell for measuring a light absorption by a sample solution in the cell comprising:
    a flow path having openings at first and second ends and being formed in a central axial portion of the cylindrical optical cell;
    a 100% reflection film covering the cylindrical outside surface of the cell other than at a light incident portion and a light output portion formed on the cylindrical outside surface; and
    a half transmitting mirror being disposed at the light output portion so as to face the light incident portion on a straight line path therewith.

15. An optical detection system for light absorption comprising:

separating means for separating a sample solution; and a cylindrical optical cell for measuring light absorption by a sample solution in the cell and for optically detecting a separated sample, the cell including a flow path having openings at first and second ends and being formed in a central axial portion of the cylindrical cell, a 100% reflection film covering a cylindrical outside surface of the cylindrical cell other than at a light incident portion and a light output portion formed on the cylindrical outside surface, and a half transmitting mirror being disposed at the light output portion so as to face the light incident portion on a straight line path therewith.

16. An optical detection system for light absorption comprising:

a sheath flow cell having a sheath flow solution inlet, a sample inlet portion, and a longitudinal cylindrical portion through which a sheath flow solution and a sample solution flow, the sheath flow cell having a light incident portion and a light output portion disposed on an outside surface of the cylindrical portion so as to face one another along a straight line path, a 100% reflection film covering the outside surface of the cylindrical portion other than at the light incident portion and the light output portion, a half transmitting mirror being disposed on the outside surface of the cylindrical portion at the light output portion so as to face the light incident portion on a straight line path therewith; and light detecting means for detecting a light passing through the light incident portion and the light output portion of the sheath flow cell for determining light absorption by the sample.

* * * * *